US00PP33832P2

(12) United States Plant Patent
Hartman

(10) Patent No.: US PP33,832 P2
(45) Date of Patent: Jan. 4, 2022

(54) ***CALADIUM* PLANT NAMED 'WQN BL V OF13-452'**

(50) Latin Name: ***Caladium* X *hortulanum***
Varietal Denomination: WQN BL V OF13-452

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 17/193,929

(22) Filed: Mar. 5, 2021

(51) Int. Cl.
*A01H 5/12* (2018.01)
*A01H 5/02* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 6/10; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Caladium* plant named 'WQN BL V OF 13-452', characterized by its intermediate and upright to mounding plant habit; dense and bushy appearance; vigorous growth habit and moderate growth rate; fancy-type leaves that are greenish white in color variably or entirely flushed with purplish red with dark greyish purple-colored venation and narrow dark green-colored margins; and petioles that are almost black in color.

4 Drawing Sheets

Figure 1:
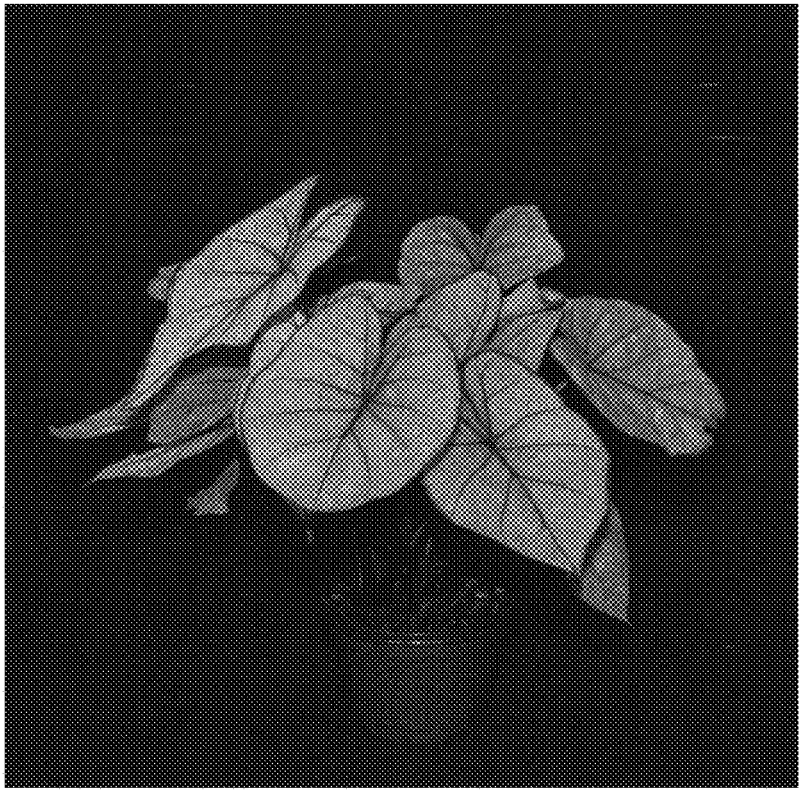

Botanical designation: *Caladium* X *hortulanum*.
Cultivar denomination: 'WQN BL V OF13-452'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'WQN BL V OF13-452'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2012 in Avon Park, Fla. of *Caladium* X *hortulanum* 'GPR SWT OF13-993', disclosed in U.S. plant patent application Ser. No. 17/013,785, as the female, or seed, parent with *Caladium* X *hortulanum* 'White Wonder', disclosed in U.S. Plant Pat. No. 21,044, as the male, or pollen, parent. The new *Caladium* plant was discovered and selected by the Inventor as a single plant within the progeny of the stated cross-pollination in a controlled outdoor nursery environment in Avon Park, Fla. in September, 2013.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2014 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'WQN BL V OF13-452'. These characteristics in combination distinguish 'WQN BL V OF13-452' as a new and distinct *Caladium* plant:

1. Intermediate and upright to mounding plant habit; dense and bushy appearance.
2. Vigorous growth habit and moderate growth rate.
3. Fancy-type leaves that are greenish white in color variably or entirely flushed with purplish red with dark greyish purple-colored venation and narrow dark green-colored margins.
4. Petioles that are almost black in color.

Plants of the new *Caladium* differ primarily from plants of the female parent, 'GPR SWT OF13-993', in the following characteristics:

1. Plants of the new *Caladium* have fancy-type leaves whereas plants of 'GPR SWT OF13-993' have strap/lance-type leaves.
2. Leaves of plants of the new *Caladium* are greenish white in color variably or entirely flushed with purplish red with dark greyish purple-colored venation and narrow dark green-colored margins whereas leaves of 'GPR SWT OF13-993' are purplish red or white predominantly and variably flushed with purplish red with dark purplish grey-colored venation and dark green-colored margins.
3. Leaf petioles of plants of the new *Caladium* are almost black in color whereas leaf petioles of plants of 'GPR SWT OF13-993' are black or brownish green in color with black-colored stippling, stripes and streaks.

Plants of the new *Caladium* differ primarily from plants of the male parent, 'White Wonder', in the following characteristics:

1. Plants of the new *Caladium* have fancy-type leaves whereas plants of 'White Wonder' have strap/lance-type leaves.
2. Leaves of plants of the new *Caladium* are greenish white in color variably or entirely flushed with purplish red with dark greyish purple-colored venation and narrow dark green-colored margins whereas leaves of 'White Wonder' are white to grey-green in color with light pink to white-colored venation and dark green-colored borders.
3. Leaf petioles of plants of the new *Caladium* are almost black in color whereas leaf petioles of plants of 'White Wonder' are tannish green with darker-colored stripes.

Plants of the new *Caladium* can be compared to plants of *Caladium* X *hortulanum* 'White Queen', not patented. In side-by-side comparisons, plants of the new *Caladium* differ primarily from plants of 'White Queen' in leaf color as leaves of the new *Caladium* are greenish white in color variably or entirely flushed with purplish red with dark greyish purple-colored venation and narrow dark green-colored margins whereas leaves of 'White Queen' are white in color with rose pink-colored venation and central areas surrounding the venation. In addition, plants of the new *Caladium* differ from plants of 'White Queen' in leaf petiole color as leaf petioles of plants of the new *Caladium* are almost black in color whereas leaf petioles of plants of 'White Queen' are black in color with tannish pink-colored stripes.

Plants of the new *Caladium* can also be compared to plants of *Caladium* X *hortulanum* 'Summer Breeze', disclosed in U.S. Plant Pat. No. 25,420. In side-by-side comparisons, plants of the new *Caladium* differ primarily from plants of 'Summer Breeze ' in leaf color as leaves of the new *Caladium* are greenish white in color variably or entirely flushed with purplish red with dark greyish purple-colored venation and narrow dark green-colored margins whereas leaves of 'Summer Breeze' are creamy white in color with central pink-colored blush, pink-colored venation and green-colored margins. In addition, plants of the new *Caladium* differ from plants of 'Summer Breeze' in leaf petiole color as leaf petioles of plants of the new *Caladium* are almost black in color whereas leaf petioles of plants of 'Summer Breeze' are tannish pink in color with faint brown-colored streaks, stippling and tessellations.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'WQN BL V OF13-452' grown in a container that has had its tuber de-eyed prior to planting.

Figure 2:
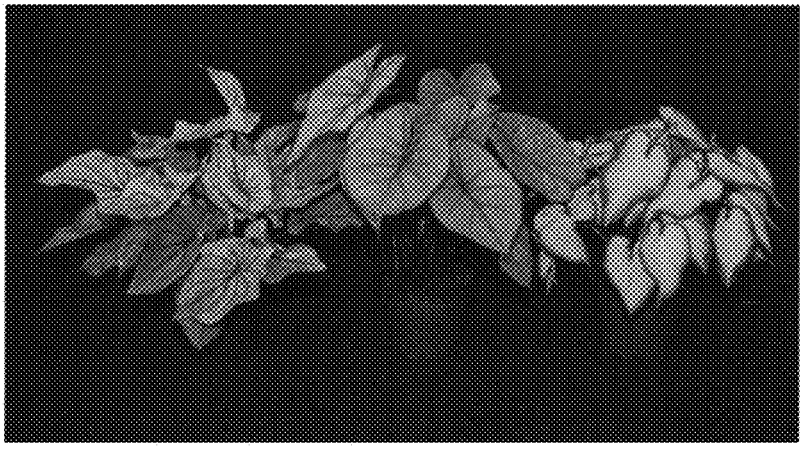

The photograph at the top of the second sheet (FIG. 2) is side perspective view of typical plants of the female parent, 'GPR SWT OF13-993' (left), 'WQN BL V OF13-452' (center) and the male parent, 'White Wonder' (right).

Figure 3:
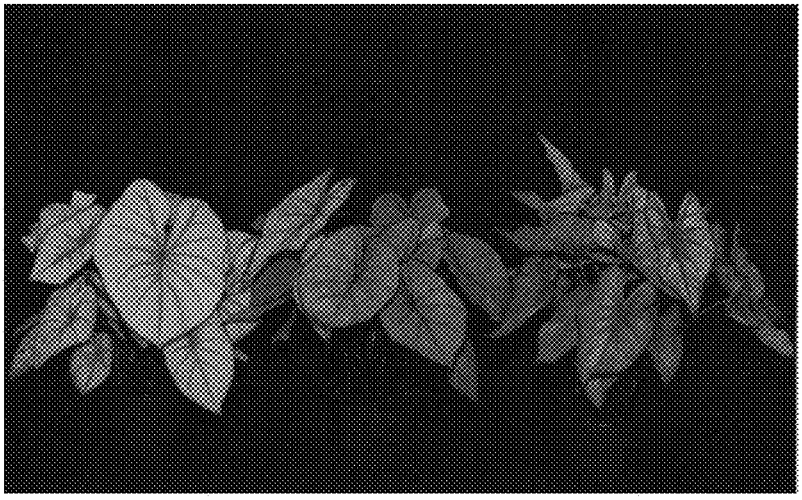

The photograph at the bottom of the second sheet (FIG. 3) is side perspective view of typical plants of 'Summer Breeze' (left), 'WQN BL V OF13-452' (center) and 'White Queen' (right).

Figure 4:
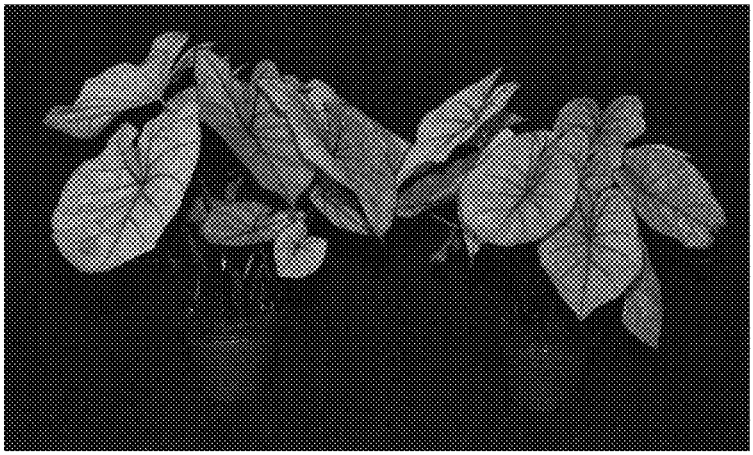

The photograph at the top of the third sheet (FIG. 4) is a comparison view of typical plants of 'WQN BL V OF13-452' grown in containers, the plant on the left has not had its tuber de-eyed and the plant on the right has had its tuber de-eyed prior to planting.

Figure 5:
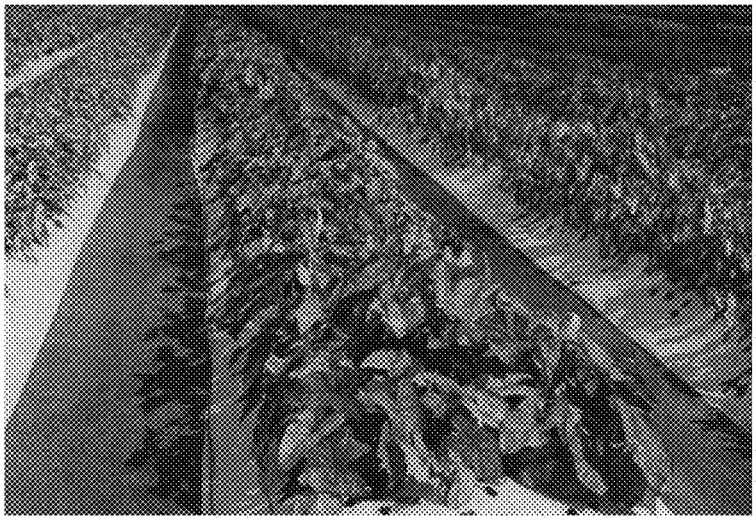

The photograph at the bottom of the third sheet (FIG. 5) is a side perspective view of typical plants of 'WQN BL V OF13-452' grown in an open production field.

Figure 6:
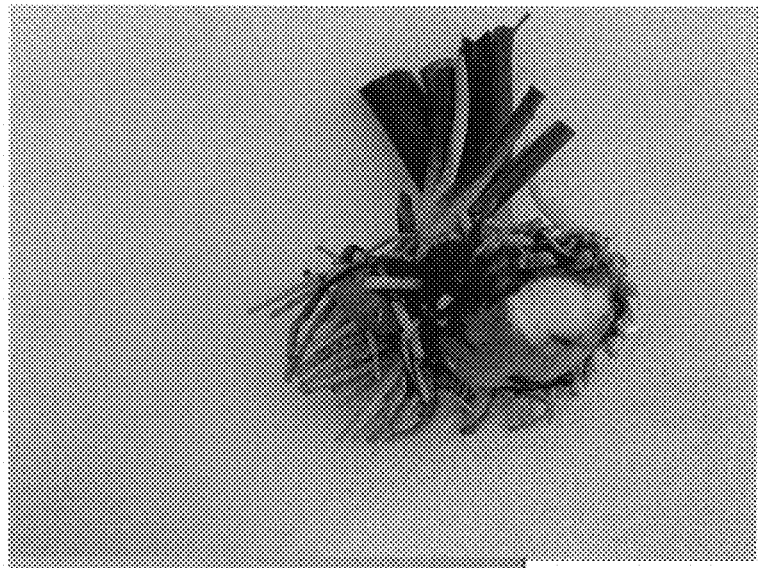

The photograph at the top of the fourth sheet (FIG. 6) is a close-up view of typical freshly-harvested tubers with roots and leaf petioles of 'WQN BL V OF13-452'.

Figure 7:
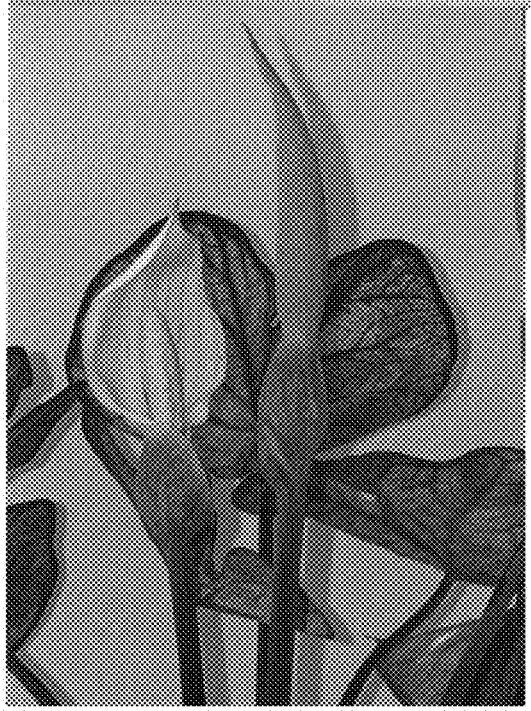

The photograph at the bottom of the fourth sheet (FIG. 7) is a close-up view of typical inflorescences of 'WQN BL V OF13-452'.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 750 μmol. During the production of the outdoor nursery-grown plants, day temperatures ranged from about 29° C. to 35° C., night temperatures ranged from about 23° C. to 26° C. and full sunlight conditions. Plants grown in the shade house were eleven weeks old and plants grown in the outdoor nursery were six months old when the photographs and the detailed description were taken. In the following description, color references are made to The Royal Horticultural Society Colour Chart, 2015 Edition, except where general terms of ordinary dictionary significance are used.

Botanical classification: *Caladium* X *hortulanum* 'WQN BL V OF13-452'.

Parentage:

*Female, or seed, parent.*—*Caladium* X *hortulanum* 'GPR SWT OF13-993' disclosed in U.S. Plant patent application Ser. No. 17/013,785.

*Male, or pollen, parent.*—*Caladium* X *hortulanum* 'White Wonder', disclosed in U.S. Plant Pat. No. 21,044.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments are elliptic in shape. Height: About 3 cm. Diameter: About 5.2 cm to 6.7 cm. Segment height: About 1.7 cm. Segment diameter: About 1.8 cm. Axillary bud shape: Roughly triangular. Axillary bud size: About 1.4 mm by 6 mm. Texture: Thick, starchy; somewhat brittle. Color: Periderm, freshly-harvested: Close to 200D. Periderm, dried: Close to 200A. Epidermis: Close to 159B and N155C. Cortical tissue: Close to 8D. Axillary buds: Close to 38C and 38D; at the edges, close to 202A. Root description: Thick, fleshy contractile roots with few lateral branches; color, close to N155C and NN155D. Rooting habit: Dense.

Plant description:

*Plant type.*—Herbaceous perennial; suitable as a potted plant in containers 15-cm to 25-cm and suitable as a landscape plant in shaded areas.

*Plant and growth habit.*—Intermediate and upright to somewhat mounding plant habit; dense and bushy appearance; vigorous growth habit and moderate growth rate; potted plants finish in saleable form in about seven weeks after planting tubers; leaf petioles and leaves arise from one or more growing points on tubers; leaf petioles initially upright and leaning outwardly with development.

*Plant height, from soil level to top of foliar plane, shade house-grown potted plants.*—When tubers are de-eyed, about 29 cm to 36 cm.

*Plant height, from soil level to top of floral plane, shade house-grown potted plants.*—When tubers are de-eyed, about 31 cm to 36 cm.

*Plant diameter or spread, shade house-grown potted plants.*—When tubers are de-eyed, about 48 cm to 52 cm.

*Number of shoots per plant, shade house-grown potted plants, tubers de-eyed.*—About two to three develop per #1 tuber.

*Number of shoots per plant, shade house-grown potted plants, tubers not de-eyed.*—About one to two develop per #1 tuber.

*Cataphylls, shade house-grown potted plants.*—Length: About 5 cm to 8 cm. Width: About 1.4 cm to 1.8 cm. Shape: Ligulate to somewhat wedge-shaped. Apex: Acuminate. Base: Sheathing the stem. Color, inner and outer surfaces: Close to 200A.

Leaf description:

*Arrangement and type.*—Alternate; simple; fancy-type.

*Length, shade house-grown potted plants, flattened.*—When tubers are de-eyed, about 20 cm to 23.8 cm.

*Width, shade house-grown potted plants, flattened.*—When tubers are de-eyed, about 12.2 cm to 15.5 cm.

*Shape.*—Ovate to broadly ovate.

*Apex.*—Acuminate.

*Base.*—Sagittate-peltate; cordate.

*Margin.*—Entire; mostly flat with broad undulations.

*Texture and luster, upper surface.*—Smooth, glabrous; dull sheen.

*Texture and luster, lower surface.*—Smooth, glabrous; glaucous; dull sheen.

*Venation pattern.*—Pinnate and palmate.

*Color, shade house-grown potted plants.*—When developing and fully expanded leaves, upper surface: Interveinal areas: Close to 157D variably or entirely flushed or mottled with close to 62D, 59C and 59D. Margins: Close to 147A tinged with close to 189A with edges, close to 187A. Basal notch: Close to 189A flushed with close to 187B. Leaf petiole junction: Close to 59C. Midvein: Close to N186B surrounded with close to 59C and flecks, close to N155C. Primary veins: Close to N186B tinged with close to 187A and surrounded with close to 59C and flecks, close to N155C. Secondary veins: Close to 147A and 139A surrounded with close to 157D. When developing and fully expanded leaves, lower surface: Interveinal areas: Close to 182D and 63B variably flushed or blotched with close to 183C. Margins: Close to 191A and 189A variably flushed with close to 183D with edges, close to 187A. Basal notch: Close to 189A flushed with close to 187A. Midvein: Glaucous, close to 183B and 183C tinged with close to 187B and surrounded with close to 183C to 183D. Primary veins: Glaucous, close to 191A and 197A variably flushed and mottled with close to 183D and 183D and surrounded with close to 183C to 183D. Secondary veins: Close to 189A, N189A, 147A and 147B surrounded with close to 183C to 183D.

*Petioles.*—Aspect: Initially upright and straight and leaning outwardly with development; flexible. Length, shade house-grown potted plants: When tubers are de-eyed, about 22 cm to 26.9 cm. Diameter, distally, shade house-grown potted plants: When tubers are de-eyed, about 3 mm to 4 mm. Diameter, proximally, shade house-grown potted plants: When tubers are de-eyed, about 6 mm to 10 mm. Texture and luster: Smooth, glabrous; glaucous; dull sheen. Color, shade house-grown potted plants: Close to 202A tinged with close to N186A with occasional streaks and stripes, close to N155C tinged with close to 182D; just below the leaf junction, same as overall colors only more glaucous. Wing length, shade house-grown potted plants: About 6 cm to 8 cm. Wing diameter, shade house-grown potted plants: When tubers are de-eyed, about 8 mm. Texture and luster, inner and outer surfaces: Smooth, glabrous; slightly glossy. Wing color, shade house-grown potted plants: Outer surface: Close to 202A and N200A; at the margins, occasional flecks and streaks, close to N155C. Inner surface: Close to N155C; center, flushed with close to N186A; venation, close to 202A; colors and patterns on the outer surface are visible on the inner surface.

Inflorescence description: Inflorescences observed on eleven week-old shade house-grown potted plants.

*Inflorescence arrangement.*—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance.*—Night-fragrant; jasmine-like with camphor note.

*Natural flowering season and flower longevity.*—Plants of the new *Caladium* typically flower during the spring and summer in central Florida; flowers develop about eleven weeks after growth commences; inflorescences last about three days before fading; inflorescences persistent.

*Spathe.*—Length, overall: About 9.8 cm. Length, distal open portion: About 6.6 cm. Length, proximal closed portion: About 3.2 cm. Width, distal open portion: About 3.8 cm. Depth, distal open portion: About 1.5 cm. Width, at constriction: About 1.1 cm to 1.3 cm. Width, proximal closed portion: About 2 cm to 2.4 cm. Shape, open portion: Ovate. Apex: Acuminate. Base: Acute. Margin: Entire; slightly reflexed. Texture and luster, front surface: Smooth, glabrous; dull sheen. Texture and luster, rear surface: Smooth, glabrous; slightly glaucous and dull sheen. Color, front surface: Distal open portion: Close to 145B; center of distal end, flushed with close to 155C to 155D; with development, color becoming closer to 155C tinged with close to 196D and faintly flushed with close to 187C; veins, tinged with close to 187B; with subsequent development, becoming closer to 199C to 199D. Proximal closed portion: Close to 147D; proximally, flushed with close to 187B; color does not change with development. Color, rear surface: Distal open portion: Close to 147C and 146C; apical streaks, close to N186C; with development, color becoming closer to 155C flushed and streaked with close to 183D. Proximal closed portion: Close to 148B and 148C with streaks and sectors, close to 147B to 147C, variably flushed, streaked, marbled or tinged with close to N186C; color does not change with development.

*Spadix.*—Length, overall: About 5.6 cm. Length, male flower zone: About 3.4 cm. Length, sterile zone: About 1 cm. Length, female flower zone: About 1.2 cm. Diameter, male flower zone: About 8 mm. Diameter, sterile flower zone: About 4.5 mm. Diameter, female flower zone: About 8 mm. Shape: Columnar, spindle-shaped. Apex: Obtuse to bluntly acute. Base: Obtuse. Aspect: Upright. Color, immature, male zone: Close to 145B. Color, immature, sterile zone: Close to 158B. Color, immature, female zone: Close to 158D. Color, mature, male zone: Close to 10C tinged with close to 1C. Color, mature, sterile zone: Close to 158D. Color, mature, female zone: Close to 155C and 155D. Male flowers: Quantity per spadix: About 125. Shape: Obovate. Height: About 2 mm. Diameter: About 2 mm. Pollen amount: Abundant. Pollen color: Close to 4C. Female flowers: Quantity per spadix: About 130. Shape: Obovate. Height: About 2 mm. Diameter: About 1 mm. Stigma color: Close to 155D. Ovary color: Close to 155C.

*Scapes.*—Length: About 21.5 cm. Diameter: About 5 mm. Strength: Sturdy; flexible. Aspect: Mostly erect, straight. Texture and luster: Smooth, glabrous; slightly glossy. Color: Close to N200A.

*Seeds and fruits.*—To date, seed and fruit development have not been observed on plants of the new *Caladium.*

Pathogen tolerance: Plants of the new *Caladium* have been observed to have average tolerance to *Pythium* Root Rot and above average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'WQN BL V OF13-452' as illustrated and described.

* * * * *